United States Patent [19]

Ericsson et al.

[11] Patent Number: 5,981,472
[45] Date of Patent: Nov. 9, 1999

[54] METHODS FOR TREATING DISEASES

[75] Inventors: Arthur Dale Ericsson, Houston; William S. Lynn, Smithville, both of Tex.

[73] Assignee: DX/IBR Corporation, Houston, Tex.

[21] Appl. No.: 08/803,619

[22] Filed: Feb. 21, 1997

[51] Int. Cl.$^6$ .......................... A61K 35/14; A61K 38/19; A61K 45/05; C12N 5/08
[52] U.S. Cl. ...................... 514/2; 514/8; 514/12; 514/885; 424/85.1; 424/85.2; 424/85.4; 435/7.2; 435/7.21; 435/7.24; 435/325; 435/372; 435/372.3; 435/375
[58] Field of Search ............................ 514/2, 8, 12, 885; 424/85.1, 85.2, 85.4, 85.5; 435/325, 372, 372.3, 375, 4, 7.2, 7.21, 7.24

[56] References Cited

U.S. PATENT DOCUMENTS 4,690,915  9/1987  Rosenberg ................................. 514/2
5,229,115  7/1993  Lynch ..................................... 424/93 V

*Primary Examiner*—Prema Mertz
*Attorney, Agent, or Firm*—John R Casperson

[57] ABSTRACT

Herein is provided a method for identifying extreme stressors which may become causative agents responsible for syndromes characterized by premature progressive cell loss or cell over growth in an individual. A sample of cells obtained from an individual is subjected to stressor in vitro to form a stressed cell sample. At least one stress criteria is measured for the stressed cell sample and the steps are repeated for a plurality of stressors. The measured stress criteria are then compared to norms derived from such measurements on cell samples obtained from third parties and a plurality of extreme stressors to which the sample of cells taken from the individual are unusually sensitive are identified. The procedure can be used to identify an effective bypass agent or needed alteration in lifestyle to prevent or delay clinical signs of disease, and/or to identify an effective bypass agent or needed alteration in lifestyle to better manage or reverse the course of the disease process.

6 Claims, No Drawings

METHODS FOR TREATING DISEASES

BACKGROUND OF THE INVENTION

Cell growth and cell death are programmed and the precise timing of each of the programs is a critical factor in the life or death of the cells of our body. Each of these life/death programs for each person is unique. This uniqueness is due, largely, in the way in which each of our genes; with their multiple mutations break and recombines together. It is the interaction of these genomes (genes) and our changing environments that will inevitably lead to the dysregulation of these multiple timing devices of all our cell types which must be maintained to protect the very delicate balance between cell growth and cell death. All of the cell types in our body grow and die at very different rates and therefore a huge number of timing devices are required to maintain homeostasis (life/death balance) between all of these different cell types. Moreover, some individual cell types survive only for a few hours while other cell types survive for years. The maintenance and regulation of this delicate balance is most difficult for the immune system (cell survival measured in hours and the nervous system (cell survival measured in years). The immune system must rapidly mobilize and proliferate in response to inflammation but it just as rapidly must demobilize and the cells must die once the crisis is past, the invaders destroyed, digested and their foreign residues are excreted or properly stored. Similarly, while the nervous system must rapidly process all incoming information and store this information or relay it to other cell in the organism. It is precisely the storage and retrieval process of the nervous system that mandates that the cells survive for years. When any toxic or metabolic mishap appears in the immune system or nervous system, then one or more programmed death programs becomes dominant.

In this age of increased communication and heightened changing environmental perturbations, these two critical systems are overworked and apt to either misread the incoming information or fail to respond to the information properly. The result is the development of symptomatic disease of multiple types and this is dependent upon the type of stress and the individual; genetic weak points that are present in our unique genomes. In most cases, death occurs, with the resultant swelling of their membrane-bound cytoplasmic granules, mitochondria and fragmentation and condensation of the nucleus. This is called apoptosis. However, occasionally, a rare over stressed cell learns how to suppress or knock out their programmed cell death, survive and amplify their own growth programs. The end result is an immortal cell, cancer.

Thus, it appears that stress induced changes in the delicate balance between cell life and cell death appears to be responsible for the chronic conditions in which the timing for cell proliferation vs. cell death becomes imbalanced and either the chronic loss or excessive accumulation of uncontrolled cells is the end result. Therefore, there are two major factors in the development of chronic diseases.

1. Stressors. These include food, especially calories or oxidants and various poisons (physical, immunologic, psychic, chemical, bacteriologic, parasitic or viral, and behavioral). The specific amount (dose) of stress that is intolerable for each specific individual must be identified.

2. Genetic weak links. These genetic factors which are responsible for the development of chronic disease are biologically trivial and, therefore, usually bypassable. Since, our over-stressed genomes have developed many routes or devices which can wither repair or develop alternate routes that bypass for the minor damages. However, in order for these alternative pathways to operate, different signals must be obtained from the living cell.

Syndromes Associated With Stressors

1. Caloric Imbalance. Calories, like all growth factors for cells, are potent activators if cell death when they are deficient (too little) or in excess (too much). When calories in excess are provided, the over worked adipocytes (fat cells), pancreatic insulin secreting cells and vascular epithelium (blood vessel lining cells) die while conversely, the cells of the colon, breast, vascular phagocytes are forced to grow excessively. The delayed symptoms that may appear include those of diabetes, fat cell death, vascular obstructions (heart and brain), immune or cerebral dysfunction and excessive cellular proliferation (cancer). The constellation of genetic weak links in each unique individual determine both the specific breaking point and the target organ system.

In the experimental model, when rodents who are deprived of motivation and supplied with an excess of food, their normal pathways that are responsible for controlling energy intake, energy usage and energy storage rapidly falter. These rodents soon degenerate. Obesity, diabetes, occluded blood vessels and excretory ducts and dysregulated cells growth disease and senility soon emerge. Not surprisingly, removal of the excess food (calories) stress prevents all of these random losses of cellular functions, including the late developing cancers. These murine experiments in caloric glut teach us that a global stress, such as energy excess, which in time results in multiple breakdowns in most of the control pathways, can be prevented by simply removing the causative energy stress plus adding a motivational component, hunger.

Undoubtably, the removal of the caloric glut along with application of living motivations in humans will slow the loss of many of our degenerating cells, especially of those cells which control our energy metabolism. However, in long lived humans, successful prevention of chronic slowly progressive cell loss/overproductive syndromes, such as atherosclerosis and cancer is difficult because it is not currently detectable at the early dpe-dysfunctional stages of the disease. Thus, to prevent these later cell losses, early detection methods are required. To perfect and quantitate such detection methods is our initial objective. Quantification is essential since each individual is unique and his response to his individual stress is also unique.

2. Oxygen. Oxygen, like calories is a potent and essential growth factor, which when taken in excess or is deficient, is rapidly fatal. When totally deficient, neurons die in 3–5 minutes and when in excess, the lining cells of the lung die within a few hours. In the metabolic consumption of calories, electrons are liberated and are capable of destroying cellular enzymes, cellular membranes (lipids and lipoproteins) as well as cellular genome (nuclear DNA). Oxygen or other electron acceptors must be available intracellularly in the appropriate amounts and the appropriate time. Furthermore, enzymes which allow oxygen to accept two electrons rather than only one must always be present and capable of functioning rapidly, especially when calories are in excess. Because superoxide and peroxide act as potential growth factors as well as potential poisons, the end result of their excess is a dysregulated oxygen metabolism which may lead to either a degenerative or proliferative disease, depending upon the genetic constitution of the individual.

3. Drugs and Addiction. Drugs, notably tobacco and alcohol damage the cellular life/death regulating systems.

Some cells proliferate excessively while the cells die and disappear. The extent of the changes in the life/death homeostatic cellular programs depends upon the individual weak links that are present in the specific cell type of each individual as well as the dose (potency) and timing of the dysregulating drug. Tobacco smoke affects the lining cells of the lungs that are necessary for the transport of oxygen and carbon dioxide into and out of the blood. Alcohol may poison the liver and a protective overgrowth of fibroblasts follow hepatocyte death.

4. Environmental Toxins. Solvents, gases, hydrocarbons, oxidants, heavy metals and many others, all effect the genetically weak link and thus are related to a dysfunction in the life/death cycle.

5. Viruses

A. The herpes virus group (herpes, Epstein Barr and other DNA viruses) lives in human cells. The prostate is commonly infected and the virus is present in the semen. The virus may cause cellar overgrowth by inhibiting one of our natural protective growth inhibitors (tumor suppressor gene, called P53) which normally inhibits cellular overgrowth. Without this effective inhibitor, the deficient cells rapidly out grow its neighboring cells and ultimately kill the surrounding cells by usurping the neighboring cells nutrition.

B. Murine retroviral model of neuro-immuno-degeneration. Injections of a murine virus, Ts1, into newborn mice results in a loss of specific immune cells and neurons with an overgrowth of astocytes in the brain in 3–5 weeks. If the animals survives the early immune and nerve cell loss, tumors of the immune system and the nervous system develop. The Ts1 virus enters its target cell by binding with the surface receptor that normally transports basic amino acids into the cell. The infected cell either multiply and produce defensive molecules or die. If the viral load is large and completely occupies all of the amino acid transporter sites on the cell membrane, the cell will either starve to death due to lack of the essential basic amino acids, especially arginine, or it will activate one of its death programs. Arginine is one of the essential amino acids that is required to produce polyamines, e.g., spermine, which amines are essential for structural integrity of the nucleus. In this murine model, the ensuing amino acid deficiencies are the crucial death factor and the predicted death may be prevented by supplying the deficient amino acids in amounts large enough to compete with the virus for transport into the cell. Furthermore, the excess amino acids that bind to the transporter will deny entrance of the virus into the cells and are potent protector agents. Moreover, in this model with imbalanced cell growth/death programs, then immune and nervous system modulators, nutritionals, anti-oxidative preventive therapies have proved to be a successful combination therapy.

Genetic Imbalance: Syndromes in which the Weak Links are Known

It is because each of us possesses unique gene pools which harbor multiple mutations that each, under stress, may activate signals which program cellular death. Therefore, we are all vulnerable to life's many stresses, especially stresses that may perturb electron flow, such as Down's Syndrome or amyotrophic lateral sclerosis syndromes (ALS). In Down's Syndrome trisomy 21, in which genes that control oxidative metabolism are imbalanced, the cell death programs, especially in the brain, are very labile and easily perturbated by most stresses. In ALS syndrome in which a major gene involved in the electron transfer (superoxide dismutase) is mutated, electron flow becomes dysregulated, especially in the very active RNA rich motor neurons. The result is that the cell death pathways are again activated and these neurons slowly degenerate.

In syndromes in which the genes that control the timing for the major activities of cells, i.e., cellular growth, death, differentiation and repair, mutagens which disrupt or imbalance these carefuilly orchestrated timing genes lead to the production of ill-formed cells with defective parts and limited survival. This fate leading to premature death is especially prominate in cells which must rapidly reproduce under stress and also must as rapidly die, such as most cells of the immune system. This type of premature death also awaits those neurons which must continuously produce and maintain cell parts, i.e., synapses and dendrites, and are, therefore, more susceptible to oxidative or metabolic stresses.

1. Ataxia Telangiectasia (AT)

AT is a syndrome in which certain cells in the immune and nervous system fail to mature properly and are eventually lost. A defective gene has been identified and it appears to function as a modulator or switching box for directing the cellular life/death process in the thymus derived T and B cells, cerebellar neurons and in some vascular cells. The result is immune deficiency, ataxia and deformed dilated blood vessels. AT is a recessive genetic disorder of childhood that occurs in one in 40,000 to 100,000 persons worldwide. At least 10% of AT patients develop cancer of the lymphoid tissues, stomach, brain, breast, skin, parotid gland, liver, larynx and ovaries. The location of the ATM gene on Chromosome 11q22-23. AT cells show increased chromosomal breakage, telomere shortening and elevated intrachromosomal recombination and are hypersensitive to ionizing radiation and radiomimetic chemicals. In ataxia telangiectasia, in which the ATN gene is mutated and fails to efficiently upregulate the major timing gene, p53, the premature death of immune cells and susceptible neurons is the end result. In those few immature cells in the thymus gland which manage to adapt to their missing timing gene (ATM), and continue to grow uncontrollably, thymic cancer in the absence of any other cancer is the end result. Furthermore, in mice, in which the ATM gene is completely knocked out, all homogenous mice, which are normal at birth, die of the thymic cancer by 4 months of age.

Since mice lacking the ATM gene from conception grow and develop normally until the thymic tumor intervenes, and since no cells other than the immature lymphocytes in the thymus either die or become cancerous, it is clear that the timing function of the ATM gene product is critical only in cells which must respond defensively to environmental stresses induced by living, i.e., cells involved in postnatal learning, immune defense and postnatal reproduction. The rapidly dividing living cells in the intestines do not degenerate but do lose their ability to defend themselves against radiant energies.

Other gene products which may disrupt the delicate balance in the cell growth and cell death pathways are abundant in man and include the presenilin genes in Alzheimer's Syndrome, the telomere genes in Huntington's Disease or AIDs, or the Fas, Fas ligands genes in murine autoimmune syndrome. In all of these syndromes, the dysregulation in the cell growth/cell death pathways leads to either excessive cell growth or to accelerated cell death, depending upon the presence of alternate or bypass pathways in the specific cell. For example, when various stresses are directed toward the central nervous system, neurons will degenerate while their more numerous support or helper cells will adapt and finally proliferate.

Progressive cerebellar ataxia and progressive oculocutaneous telangiectases appear at the ages of 2–6 in the affected children. Elevated serum alphafetoprotein and plasma carcinoembryonic antigen combined with low levels of IgA and/or IgE provide the laboratory basis for the clinical picture of AT.

2. Down's Syndrome (Trisomy 21)

One extra chromosome is present and too much DNA is present in each cell and the resultant dysregulated signaling also leads to either cell death or uncontrolled cell growth. The premature neuronal cell death in Down's Syndrome can be completely prevented, in vitro, by supplying the cells with extra reductants and/or antioxidants. Thus, although the precise function of all the excess normal genetic material is not known, it is clear that the loss of neurons is due at least in part either to a deficiency in reductive energy or to an excess of oxidizing power. The extra copy of chromosome 21 may lead to the development of Alzheimer's/Parkinson's Disease pathology is that the gene leads to the over production of amyloid and the accumulation of senile plaques, 3. Cancer Cancer is an imbalance of Life/Death programs:

a. Life/death balancing factors in which stimulators such as c-mye, cyclin, D1, AP-1, Il-2, and E1A, TGFa are opposed by P21, p53, Rb, Fas, Stromelysin and TGFb.
b. Energy Homeostasis (calories, fatty acids, etc.)
c. Redox Homeostasis (cysteine, NO)
d. Proteolysis Homeostasis (Ice, CPP32, Stromelysin)
e. Nutrient Homeostasis(choline, arginine)
f. Transport Homeostasis
g. Nuclear Structure Homeostasis
h. Basal Membrane Homeostasis (differentiation, apoptosis)
i. Plasma Membrane Homeostasis (ligands, matrix, signal transduction)
j. Cell Cycling Homeostasis (Cyclin, p21, c-myc, WAF1, ICE)
k. Basement Membrane (Matrix) Homeostasis.

The C-myc primary gene which is responsible for maintaining the cellular life/death balance, while Cyclin-D1 is an enzyme that is required during mitosis. E1, AP1, TGFs, IL-2 and the basement membrane are some of the known growth factors which are required for cells to grow and differentiate into mature cells. P21, p53, Rb, Fas, TGFb are factors that stop cellular growth and cellular cycling. Stromelysin is a proteolytic enzyme that destroys the basement membrane and thus removes the major required for cell differentiation. Spermine is a highly charged growth factor which is used to stabilize the ever changing structure of DNA and various other structural proteins and lipids. p34 is a factor required to stabilize the nuclear components to be reproduced during cell cycling (mitosis).

Signal Transduction Imbalances

Viruses, which must bind to specific receptors or transporters on the surface of cells for entry and exit from specific cells and they also must usurp the cell's growth machinery for its own parasitic reproduction and will eventually perturb the cell's growth/death pathways with subsequent uncontrolled cell growth and/or cell death.

Viruses also disrupt cellular growth/death pathways by inserting their own promotional genes into inappropriate locals in the host DNA. This insert, like other agents which may oxidize or change or damage host DNA, may activate the cell death pathways. Such activated pathways may be beneficial in the sense that unwonted viruses or cancerous cells or overactive destructible inflammatory cells can be eliminated. But perturbation of this cell destruction process will in time result in the cell loss syndromes as seen in neuro-immuno-degenerative disorders or aging.

There examples suggest that most of our current chronic ills result form aberrant signals induced by mutated genes or destructive environmental cues which perturb timing of the cell growth/cell death pathways. These examples also suggest that if counter signals which can rebalance these uncontrolled pathways were available, most of our degenerative and neoplastic illnesses could be avoided.

OBJECTS OF THE INVENTION

1. To identify, pre-clinically, those sub-clinical genetic and environmentally induced proclivities responsible for syndromes of premature progressive cell loss/over growth.

2. To monitor the course of therapeutic interventions which may bypass and prevent such cell loss/overgrowth.

3. To exploit current life style experimentation's to accomplish objective number 1.

4. To utilize individual circulating immune cells under a variety of stresses as our primary indicators or and the monitors for sub-clinical degenerative, either proliferative or apoptotic, syndromes.

SUMMARY OF THE INVENTION

In one embodiment of the invention, there is provided a method for identifying extreme stressors which may become causative agents responsible for syndromes characterized by premature progressive cell loss or cell over growth in an individual. The method is carried out by obtaining a sample of cells from the individual. The sample of cells is subjected to a stressor in vitro to form a stressed cell sample. At least one stress criteria is measured for the stressed cell sample. These steps are repeated for a plurality of stressors. The measured stress criteria are then compared to norms derived from such measurements on cell samples obtained from third parties. From the comparison, a plurality of extreme stressors to which the sample of cells taken from the individual are unusually sensitive compared to the norms can be identified.

The above described procedure can be applied to either asymptomatic individuals or individuals who show clinical signs of disease process. For asymptomatic individuals, the procedure can be used to identify an effective bypass agent or needed alteration in lifestyle to prevent or delay clinical signs of disease. For symptomatic individuals, the procedure can be used to identify an effective bypass agent or needed alteration in lifestyle to better manage or reverse the course of the disease process. An effective bypass agent may be identified by subjecting the stressed cell samples to a plurality of bypass agents and then remeasuring the stress criteria for each sample. An effective bypass agent can then be identified from the thus generated data and administered to the individual.

In another embodiment of the invention, there is provided a method for monitoring the response of an individual to intervention steps taken to alleviate the propensity of extreme stressors to cause syndromes characterized by premature progressive cell loss or cell over growth in said individual. The method is carried out by establishing baseline measurements for a plurality of stress criteria from the individual's cell samples stressed under in vitro conditions. A plurality of extreme stressors for that particular individual are then identified by comparing the baseline measurements to norms derived from baseline measurements on third parties. Intervention steps are then prescribed to alleviate the propensity of the thus identified extreme stressors to cause the above-noted syndromes. At a subsequent time, follow up is provided by obtaining a sample of cells from the individual and obtaining new measurements in vitro for at least a portion of the stress criteria for the plurality of the previously identified extreme stressors. The newly measured stress criteria are compared to the previously obtained baseline measurements in order to monitor the response of the individual to the intervention steps.

In order to prevent disease, the two major requirements are:

1. Early recognition, before any symptoms, of the presence of inciting stressors, i.e., mutant genes, viruses, habits, societal and spiritual stressors, etc.

2. Methods to monitor the progress of any therapeutic attempts which either remove or successfully bypass the injurious stressors. To supply these requirements to the public is the goal of this invention.

Because the major function of the immune system is to daily supply a homeostasis, a balance, between the stressors and the weak links (genetic alterations) and the methods to serially monitor these immune responses in response to injury are rapidly becoming available, it is the intent to utilize these very sensitive recognition tools of each individual's circulating immune cells to supply us with both recognition of the stressors, responses of the immune cells in culture and to monitor the therapeutic attempts to prevent the alterations in the cultures. Armed with this type of individualized information, each of us could evade our stressors and plan more effectively, our daily experiments in living and thereby evade the premature losses of specifically injured cells and organs. In this way, all of our various cell types could live in harmony with each other and die at rates compatible with their replacement rates. There would be no cell losses and disease would be significantly reduced.

DETAILED DESCRIPTION OF THE INVENTION

In one embodiment of the invention, there is provided a method for identifying extreme stressors which may become causative agents responsible for syndromes characterized by premature progressive cell loss or cell over growth in an individual. The method is carried out by obtaining a sample of cells from the individual. The sample of cells is subjected to a stressor in vitro to form a stressed cell sample. At least one stress criteria is measured for the stressed cell sample. These steps are repeated for a plurality of stressors. The measured stress criteria are then compared to norms derived from such measurements on cell samples obtained from third parties. From the comparison, a plurality of extreme stressors to which the sample of cells taken from the individual are unusually sensitive compared to the norms can be identified.

In a preferred embodiment the sample of cells is taken from the individual's circulating immune cells. Preferably, lymphocytes such as B and T lymphocytes are used. More preferably, the T cells are further divided on the basis of expression of the co-receptor proteins CD4 and CD8.

The selected cells are cultured in vitro. Preferably, a plurality of cells cultures is used. The cultured cells are subjected to various stressors in order to determine how they respond to the stressor. The stressor can selected from the group consisting of a caloric glut, an oxidant, an antioxidant, a drug, a poison, ionizing radiation, an enzyme, and a growth factor, for example. Examples of stressor drugs are alcohol and various components of tobacco smoke such as nicotine, for example. Examples of poisons are solvents, gases, various hydrocarbons, and metals, particularly heavy metals. Growth factors can be selected from cell life factors and a cell death factors. Examples of cell 1 life factors are c-mye, cyclin, D1, AP-1, Il-2, and E1A, TGFa. Examples of cell death factors are P21, p53, Rb, Fas, Stomelysin and TGFb.

The stressed cell cultures can be evaluated according to a number of stress criteria. Energy homeostasis can be evaluated by using calories or fatty acids as the stressor. Redox homeostasis can be evaluated by using cysteine or NO as the stressor. Proteolysis homeostasis can be evaluated by using ice, CPP32 or stromelysin as the stressor. Nutrient homeostasis can be evaluated by using choline or arginine as the stressor. Cell cycling homeostasis can be evaluated by using cyclin, p21, c-myc, WAF1, or ice as the stressor. Other stress criteria which may be evaluated include transport homeostasis, nuclear structure homeostasis, basal membrane homeostasis, cell differentiation, cell apoptosis, plasma membrane homeostasis, basement membrane homeostasis, and ligands, matrix, and signal transduction, for example.

In another embodiment of the invention, the above described procedure can be applied to either asymptomatic individuals or individuals who show clinical signs of disease process. For asymptomatic individuals, the procedure can be used to identify an effective bypass agent or needed alteration in lifestyle to prevent or delay clinical signs of disease. For symptomatic individuals, the procedure can be used to identify an effective bypass agent or needed alteration in lifestyle to better manage or reverse the course of the disease process. An effective bypass agent may be identified by subjecting the stressed cell samples to a plurality of bypass agents and then remeasuring the stress criteria for each sample. An effective bypass agent can then be identified from the thus generated data and administered to the individual.

As an example, this aspect of the invention is expected to have good applicability to individuals afflicted by gene-related syndromes such as Ataxia Telangiectasia or Down's Syndrome.

The cell samples employed are preferably lymphocytes, such a T cells. The cells are stressed by culturing in the presence of a variety of stressors. Examples of stressors are free radicals and neurotoxic inflammatory products such as TNF, IL-1, or Fas ligand. The cells can also be stressed in the presence of a polyclonal mitogen such as phytohemagglutinin or Pokeweed mitogen. The mitogen can be employed together with a limiting amount of autologous serum. Other stressors include NTF alpha, TGF beta, cyclosporin, and ceramide.

Various stress criteria can be used to evaluate the effect of the stressor. Examples of stress criteria include the rates of cell proliferation, homotype aggregation and cell death the stress criteria can target specific cells, such as antigen-specific T cell proliferation, or some function of specific cells, for example a T cell effector function, such as growth rate, death rate, death rate type, target cell killing, CD changes, macrophage activation, B cell activation and lymphokine production. Specific examples include measuring CD8 T cell function by the killing of target cells by cytotoxic T cells, or measuring CD4 T cell function by the release of cytokines or cytotoxins.

Examples of bypass inducing agents include interleukin 2, interleukin 6, interleukin 12, interferon gamma, fatty acid binder, cell-matrix component, free radical buffer, and redox modulator such as N-acetyl cysteine, melatonin, catalase or hydrogen peroxide are suitable.

In another embodiment of the invention, there is provided a method for monitoring the response of an individual to intervention steps taken to alleviate the propensity of extreme stressors to cause syndromes of premature progressive cell loss or over growth in said individual. The method is carried out by establishing baseline measurements for a plurality of stress criteria from the individual's cell samples stressed under in vitro conditions. A plurality of extreme stressors or that particular individual are then identified by comparing the baseline measurements to norms derived from baseline measurements on third parties. Intervention steps are then prescribed to alleviate the propensity of the thus identified extreme stressors to cause syndromes of premature progressive cell loss/over growth in that individual. At a subsequent time, follow up is provided by obtaining a sample of cells from the individual and obtaining new measurements in vitro for at least a portion of the stress criteria for the plurality of the previously identified extreme stressors. The newly measured stress criteria are compared to the previously obtained baseline measurements in order to monitor the response of the individual to the intervention steps.

EXAMPLES

Preliminary Data

1. Ataxia Telangiectasia

Our studies on several murine and human model systems of neuro-immuno-degeneration, in neurons and lymphoid immune are the cells primarily affected strongly suggest that extended signaling molecules which can block or bypass the pathways responsible for the premature death of the immune cells and neurons do exist. For example, in lymphocytes which circulate in the AT syndrome and which fail to express appropriate surface adhesive markers or to produce enough of their essential survival or growth factors when stressed by culturing, we showed that the ATM-deficient cells could grow and function normally if supplied with the appropriate mix of counter signals which override the cell's death signals. These protective signals include interleukin 2 (IL-2), interleukin 6 (IL-6), interleukin 12 (IL-12), interferon gamma, fatty acid binders, cell-matrix components as well as free radical and redox buffers. Thus, it appears that with deficiency in the ATM-dependent timing of cell proliferation, defective cells lacking those defenses which are required only under postnatal stresses, accumulate in vivo. These observations indicate that application of these counter signals in the AT syndromes could prevent the inevitable immune-deficiency, as well as the lymphoid cancers. Furthermore, the chronic neuronal degeneration in AT may also be preventable. Our recent data also suggest that the neuronal degeneration is, at least in part, secondary to the immune dysfunction in the brain with over production of free radicals and other neurotoxic inflammatory products including TNF, IL-1, and Fas ligand by the uncontrolled immuno/inflammatory system in the brain. Moreover, the T cell deficiency caused by the AIDS virus may also result in neuronal degeneration due to imbalanced immune/inflammatory function in the brain. The loss of T cell suppressor activity via IL-4 in the brain which results in the production of neurotoxic over activity by the resident infected macrophages-astrocytes in brain is like responsible for the neuronal losses in AIDS dementia.

2. Murine Virus-induced Neuro-immuno-degeneration

Infection of one strain of one day old FVB mice with retrovirus MoMuLV (Tsi) results in the loss of lymphoid cells in the thymus and spleen as well as loss of the motor neurons in the brain stem and spinal cord by 6 weeks of age with concomitant severe muscle and fat tissue wasting. This virus infects and kills lymphoid cells and activates cells of the macrophage type, including the immune cells, (astroglia and microglia), in the brain. The result of the over activity of the astroglia in the brain is the accumulation of astrocyte-derived neurotoxins, tumor necrosis factor alpha, Fas receptor and IL-1. These cytotoxins cause neuronal and myelin degeneration in the brain stem and cerebellum. The wasting in the mice is likely the result of the inhibition of the expression of the anabolic enzymes in adipose tissue and muscle by the astrocyte/macrophage-derived cytotoxins, such as lymphotoxins and cytokines. Whether lymphocyte-derived cytoxins, such as lymphotoxins alpha are also involved in the process of wasting and cell losses has not yet been established.

As that seen in the AT model, these Tsi-infected mice will, in time, develop lymphoid (thymic-derived) cancers if the viral load is low and provided that the rate of immune and neuronal cell loss is low and not, in itself, fatal.

These observations suggest that imbalances, as seen in either the AT or in HIV infection models in mice, in the immune-inflammatory system are largely responsible for the dysregulated cell growth/cell death pathways in both lymphocytes and neurons. The implication of this finding is that prevention of these cell losses by counter signals which can block or redirect the cell death pathways is possible. Furthermore, using the Tsi model, we have been partially successful in identifying multiple signals which, in vivo, can prevent the neuronal and immune cell losses and delay, but not prevent, the terminal cancer. These, in vivo, preventive signals include the super adjuvant, polyinosine-cytosine (which is a powerful immune stimulant), TH1-type cytokines (IL-2 and alfa interferon) and redox agents (N-acetyl cysteine and melatonin). Moreover, all of these signals have been shown to block cell death of mitogenically activated infected splenocytes, in vitro. However, the addition of TH2-type cytokines (IL-4, IL-10 and IL-6) were required to prevent the cell death. The redox agents accelerated the rate of thymocyte cell death. Very high concentrations of autologous serum or calf serum were found to prevent the mitogen-induced death of both cell types. Serum, therefore, appears to contain the appropriate balance of both survival factors and growth factors for both mature and immature lymphoid cell types.

These data further indicate that the signals to counteract, both in vivo and in vitro, the mitogen induced cell death pathways in murine lymphocytes do exist and are available for therapeutic application, in man. However, a more effective therapy for AT may be to target the ATM gene into host autologous stem cells and implant these ATM cells back into the subject. If this hypothesis is correct, then the neuronal degeneration is secondary to the immune imbalance and, therefore, correction of the immune balance would prevent the subsequent death of neurons.

3. Neuroimmuno Degeneration in the Wasted Mouse

The loss of neurons and lymphocytes which occurs at 4–5 weeks of age in the "wasted" mouse syndrome closely resembles that seen in the Tsi-infected neonatal mice, except that an unknown gene is responsible. Wasting in the "wasted" mouse syndrome is associated with a loss of muscle, splenocytes and adipose tissue, but without a decrease in food intake, and this appears in the mice at 3–4 weeks of age The more mature splenocytes, in contrast to the immature lymphocytes, disappear rapidly in the wasted mouse. Increased expression of macrophage products, TNF and IL-1 has been found, without and influx of peripheral inflammatory cells and these are found in the brain in this wasted mouse model. On the other hand, increased expression of TNF mRNA in lymphoid organs was not observed Furthermore, in contrast to the "wasted mouse" model, expression of lymphocyte-derived or macrophage-derived cytokines was not observed by us in the atrophic lymphoid organs of the Tsi-infected mice.

However, in our studies on the splenocytes and thymocytes of the "wasted" mouse model, we did observe that these lymphoid cells were, like the Tsi-infected cells, very labile and failed to aggregate when mitogenically activated but rather rapidly activated their cell death pathways. Similarly, lymphoid cells, isolated from mice in which the ATM gene had been knocked out, were shown to rapidly undergo apoptotic cell death in culture. Cell surface maturation markers, CD3, CD4, and CD8 were severely depleted in the ATM-deficient lymphocytes but not in the "wasted: mice splenocytes. Thus, the "wasted" mouse cells, suddenly die postnatally. The losses of the non-immune cells, is likely to result, as in the AT, Tsi and HIV mouse models, of the imbalanced immune cell functions. In the "wasted" syndrome, the cell death pathway in mature T cells becomes activated, whereas, in the AT and Tsi syndromes, the cell death pathway is activated in the immature T cells. In all cases the loss of the mature T cell functions appears to be a primary factor involved in loss of function of the non-immune cell types.

The above findings indicate that the blockage of terminal differentiation with liberation of apoptosis-prone and immature lymphoid cells, is the common feature in both the virus and gene-induced syndromes of neuroimmuno-degeneration and neoplasia. These findings further suggest that these pathways to premature cell death can be controlled and the cell death may be prevented by application of appropriate external counter controls. Moreover, the ability of the stressed T cells to produce their own survival factors, in vitro, can be used as indicators of the extent of the disease as well as may be employed as monitors for the disease progression or reversal during therapy and life style changes.

Experimental Procedures and Analysis
Lymphocyte and/or T-Cell Activation

Lymphocytes and T Cells circulate throughout the body as sensors of both internal environment as well as invasions from the outside environment. Lymphocyte activation and proliferation is initiated in the lymphoid tissues where the antigen is trapped by specialized cells. The three main types of specialized antigen presenting cells are macrophages, dendritic cells and B cells. Only these express the specialized co-stimulatory molecules the enable them to activate the naive T cells. These display the antigen to the naive circulating lymphocytes as they migrate through the lymphoid tissue before returning to the bloodstream via the lymphatic channels. Upon recognizing its specific antigen, the small lymphocyte stops migrating and enlarges. The chromatin in its nucleus becomes less dense, nucleoli appear, the volume of cytoplasm increases and new RNA and protein synthesis are induced. At this stage the cells are called lymphoblasts. The cell begins to divide, normally duplicating two to four times every 24 hours for three to five days, so that the original lymphocyte may give rise to a clone of around 1000 daughter cells of identical specificity. These then differentiate into effector cells capable of secreting a specific antibody or in the case of B and T cells capable of destroying infected cells or to activate other cells of immune system. Signaled by the cytokines produced by inflammatory cells, lymphocytes, along with adhesion molecules on their surface membranes, migrate to the infection. Activation of the naive T cells requires the recognition of a foreign peptide fragment bound to a self MHC molecule and a co-stimulatory signal by a specialized antigen-presenting cell (APC). Increases of T cells production may also arise from the activation of specialized receptors for the specific cytokine. Therefore, The T-Cell responds to a specific activating stimulus (stressor) and in culture grows, dies, alters its membrane (CD) and produces cytokines.

1. Lymphocyte (T Cell) Separation

The process of analysis of cultures from lymphocytes is relatively easy. The first step is to isolate lymphocytes form whole blood by using a density centrifugation over a gradient of Ficol and metrizimide. This yields a population of mononuclear cells at the interface that has been depleted of red blood cells and most of the polymorphonuclear leukocytes or granulocytes. The residual consists mainly of lymphocytes and monocytes. Resting lymphocytes present a uniform appearance and are small round cells with a dense nucleus and very little cytoplasm. This uniformity is deceiving, because these cells comprise many different sub-populations. These are distinguished on the basis of their differential expression of cell-surface proteins, which can be detected by the use of specific antibodies. B and T lymphocytes may be identified and separated from each other by antibodies to the constant regions of the B and T cell receptors. Furthermore, the T cells are further divided on the basis of expression of the co-receptor proteins CD4 and CD8. Studies on isolated lymphocytes populations have shown that lymphocytes bearing particular combinations of surface proteins have particular finctions. For this reason the groups of surface molecules are called clusters of differentiation (CD).

2. Lymphocyte (T Cell) Culture

Certain substances induce many or all lymphocytes of a given type to proliferate. These substances are referred to as polyclonal mitogens because they induce mitosis in lymphocytes of many different species or clonal origins. Phytohemagglutinin (PHA) and Concanavalin A (ConA) stimulate T cell proliferation in the human and mouse, respectively. Conversely, Pokeweed mitogen (PWM) appears to stimulate the growth of B and T cells. Although the polyclonal mitogens do not act directly on the antigen specific receptors of lymphocytes, the appear to trigger the same growth response mechanisms as antigen. Once the lymphocyte culture has been optimized using the proliferative response to polyclonal mitogens, it is possible to detect antigen-specific T cell proliferation by measuring the thymidine uptake, for example, in response to antigen to which the T cells donor had been previously immunized.

3. Measurement of T Cell Function

Effector T cells are detected by their effects on target cells that display a specific antigen. Measuring these effector functions forms the basis of T cell bioassays which are used to assess both T cell specificity for an antigen and T cell effector functions. In general T cell effector functions may be measured by 1. Growth rates, 2. Death rates and type, 3. Target cell killing, 4. CD changes, 4. Macrophage activation, 6. B cell activation and 7. Lymphokine production.

CD8 T cell function is usually determined using the simplest and most rapid T cell assay; the killing of a target cell by a cytotoxic T cell. This may be detected by the use of radioactive chromium release assay. Proliferating target cells may be labeled with thymidine which is incorporated into the replicating DNA. On attack by the cytotoxic T cell, the DNA of the target cell is rapidly fragmented and the thymidine may be measured in the supernatant. The fragmentation of the DNA results from the induction of apoptosis. Nucleotides may be added and bind to the free ends of the DNA which provides the basis for the dUPT-biotin nick end labeling or TUNNEL assay.

CD4 T cell function involves the activation rather than the killing of cells bearing specific antigens. Macrophages may be activated by CD4 T cells or T cells that recognize other antigens on the macrophage cell surface. Other CD4 T cells induce B cells to secrete specific antibodies and these production may serve as the basis for an assay. These T cell effector functions are mediated by non-specific mediator proteins called cytokines and cytotoxins which are released by the T cell when it recognizes and antigen. As different T cells release different amounts and types of cytokines or cytotoxins it is possible to measure the protein it produces. These cytokines may serve as growth factors or inhibitors or by modification of ELISA; known as sandwich ELISA. It derives its name from the fact that the cytokine is characterized by its ability to bridge between two monoclonal antibodies reacting with different epitopes on the cytokine molecule. Moreover, a slightly different technique, the ELISPOT assay may be used to detect specific antibody secretion by B cell. Bioassays must always be confirmed by inhibition of the response with monoclonal antibodies against the cytokine.

4. T Cell Response to Stresses

Since it is now clear that all of us harbor multiple mutations which are uniquely our own and which may be expressed postnatally in our rapidly adapting dividing T cells, it is likely that any functional changes, or weak-links, that can be induced when genetic alterations are induced and detected in activated T cells which are stressed and run at high speeds for long periods of time. Also, by varying the stress, the speed or the time, one can quantitate performance of the weak-link. Because the weak-link must be relatively trivial, since the individual is not only alive but gross symptoms have not surfaced, the chance of finding the appropriate bypass signals using damaged immune cells are excellent.

5. T Cell Stresses/Assays

A. Routine initial assays

After isolation, the subject T cells are routinely stresses by adding various mitogens along with limiting amounts of autologous serum. Rates of cell proliferation, using thymidine uptake, homotype aggregation and cell death are monitored daily. These assays are all done in the presence and in he absence of combinations of various survival factors, including IL-1, IL-2. IL-4, IL-6, IL-7, IL-10, IL-12 and Interferon alfa. Sensitivity of the cells to various inhibitory signals, TNF alpha, TGF beta, cyclosporin and ceramide are also evaluated.

All of the above assays are also done in both the presence and absence of various redox modulators, including N-acetyl cysteine, melatonin, catalase and H202. Oxidants are used to activate the acute phase defenses by the activation of the cells by NFKB and p53. These two genes are the major control points for both the acute phase and apoptosis activation, as well as, for the temporary inhibition of cell cycling with activation of DNA repair.

B. Subsequent assays-dependent upon the outcome of the routine assays

1. Rates of exposure of the membrane phosphatidyl serine using either Annexin or Mc540 as indicators 2. Mitochondrial membrane potential. This is assessed using cyanine dye, DiOC 6, both on freshly isolated cells and after stressing the cells by either serum deprivation or by TNF alpha.

3. Accumulation of the apoptosis inducer, ceramide, is measured after stressing the cells, either by serum deprivation or by Fas ligand or by TNF alpha.

4. Secretion of the TH1 and TH2 cytokines, primarily IL-2, IL-12, IL-6, IL-4, and IL-10, after mitogenic activation in serum deprived media.

5. Surface markers, primarily CD3, CD4, CD8, CD69, CD40, FAS and TNF receptors, p55, and p75. Adhesions, primarily ICAM and cadherin, will be assessed in any cells found to be defective in their ability to homotypically aggregate while mitogenically activated.

6. Apoptosis Vesiculation and Cell Cyding Assay

This is performed on serum depleted lectin activated cells after fixation and labeling of the DNA with propidium iodide. The cells and vesicles are then sorted by size and content of intact and fragmented DNA as estimated fluorimetrically. The large cells in G2, the normal sized cells in G1-S and the small cells (vesicles) containing fragmented DNA are enumerated at 24 and 48 hours post incubation. Since this type of cell death usually involves the proteolytic cleavage of nuclear components (lamin and polymerase (adenosine diphosphate-ribose), these apoptotic assays are all done in the presence and absence of ICE-specific protease inhibitors. This type of assay is most useful, in our evaluation, of the many types of T cells which circulate and which are rapidly changing in response to the environmental or therapeutic inducers under study.

7. Redox Status

Production, during stress, of protein carbonyls, lipid peroxidation and DNA oxidation products (8-OH cytosine) is assayed over time in these isolated T cells. These assays are done in the presence and absence of TH1 cytokines, N acetyl cysteine, melatonin, Picnogenol, catalase and H202.

8. Transcription Factors

Since the products of two genes, NFKB and p53, are the two major factors involved in cellular responses to most types of injury or stress, their activation will be assessed over time in these stressed T cells.

While certain preferred embodiments of the invention have been described herein, the invention is not to be construed as so limited, except to the extent that such limitations are found in the claims.

What is claimed is:

1. A method for treating disease in an individual having Ataxia Telangiectasia by blocking or bypassing pathways responsible for premature cell death, said method comprising a.) obtaining a sample of lymphocytes from the individual;

b.) subjecting said lymphocytes to a stressor in vitro to form a stressed cell sample, wherein the lymphocytes are stressed by culturing;

c.) measuring a stress criteria for the stressed cell sample, wherein the stress criteria is selected from the group consisting of energy homeostasis, redox homeostasis, proteolysis homeostasis, nutrient homeostasis, cell cycling homeostasis, transport homeostasis, nuclear staructure homeostasis, basal membrane homeostasis, cell differentiation, cell apoptosis, plasma membrane homeostasis, and basement membrane homeostasis;

d.) subjecting the stressed cell sample to the presence of a bypass inducing agent;

e.) remeasuring the stress criteria for the stressed cell sample in the presence of the bypass inducing agent;

f.) repeating steps d.) and e.) for a plurality of bypass inducing agents and generating data;

g.) analyzing the thus generated data to identify an effective bypass inducing agent; and h.) administering, to the individual, the thus identified bypass inducing agent;

wherein the bypass inducing agent is selected from the group consisting of interleukin 2, interleukin 6, interleukin 12, interferon gamma, fatty acid binder, cell-matix component, free radical buffer, and redox buffer.

2. A method as in claim 1 wherein the stressor is selected from the group consisting of free radicals and neurotoxic inflammatory product.

3. A method as in claim 2 wherein the neurotoxic inflammatory product is selected from the group consisting of TNF, IL-1, and Fas ligand.

4. A method as in claim 1 wherein the lymphocytes are T cells.

5. A method as in claim 4 wherein the stress criteria comprises at least one T cell effector function selected from the group consisting of growth rate, death rate, death rate type, target cell killing, cluster of differentiation changes, macrophage activation, B cell activation and lymphokine production.

6. A method as in claim 5 wherein the stress criteria comprises CD4 T cell function as measured by release of cytokines or cytotoxins.

* * * * *